United States Patent
Campbell et al.

[11] Patent Number: 5,915,072
[45] Date of Patent: Jun. 22, 1999

[54] INFRARED HEATER APPARATUS

[75] Inventors: John Stephen Campbell, Florence, Ky.; Charles Goldberg, Cincinnati, Ohio

[73] Assignee: Hill-Rom, Inc., Batesville, Ind.

[21] Appl. No.: 08/853,040

[22] Filed: Apr. 30, 1997

[51] Int. Cl.[6] ............ F21V 31/02; F21V 25/12; H05B 3/44
[52] U.S. Cl. ............ 392/418; 392/408; 392/415; 219/411; 219/553; 250/504 R
[58] Field of Search .......... 392/418, 416, 392/407, 408, 415; 219/553, 411; 250/504 R; 313/110, 112; 600/22, 21; 607/100, 88, 90, 91

[56] References Cited

U.S. PATENT DOCUMENTS

| | | | |
|---|---|---|---|
| 3,646,319 | 2/1972 | Auld | 392/423 |
| 4,064,402 | 12/1977 | Posnansky | 250/504 R |
| 4,818,849 | 4/1989 | Matlen | 392/411 |
| 5,162,038 | 11/1992 | Wilker | 392/418 |
| 5,382,805 | 1/1995 | Fannon et al. | 250/504 R |
| 5,453,077 | 9/1995 | Donnelly et al. | 600/22 |
| 5,474,517 | 12/1995 | Falk et al. | 600/22 |
| 5,498,229 | 3/1996 | Barsky et al. | 600/22 |

FOREIGN PATENT DOCUMENTS

| | | | |
|---|---|---|---|
| 508667 | 7/1953 | Belgium | 600/22 |
| 619995 | 10/1994 | European Pat. Off. | 600/22 |
| 1229453 | 9/1960 | France | 392/407 |
| 63-281181 | 11/1988 | Japan | 392/408 |
| 1-35887 | 2/1989 | Japan . | |
| 1-67885 | 3/1989 | Japan | 219/553 |
| 2-236987 | 9/1990 | Japan | 219/553 |
| 3-30277 | 2/1991 | Japan | 219/553 |
| 6-134040 | 5/1994 | Japan . | |
| 908793 | 10/1962 | United Kingdom | 392/408 |

*Primary Examiner*—Philip H. Leung
*Assistant Examiner*—J. Pelham
*Attorney, Agent, or Firm*—Barnes & Thornburg

[57] ABSTRACT

A radiant heater apparatus includes a heating element which generates radiant energy. The heating element has first and second terminals. The apparatus also includes an inner tube configured to surround the heating element. The inner tube includes first and second ends. The inner tube is substantially transmissive to radiant energy. The apparatus further includes an outer tube surrounding the inner tube. The outer tube has an inner surface, an outer surface, and first and second ends. The inner surface of the outer tube is absorptive to radiant energy, and the outer surface of the outer tube is emissive to radiant energy so that radiant energy from the heating element passing through the inner tube is absorbed and re-emitted from by outer tube.

44 Claims, 7 Drawing Sheets

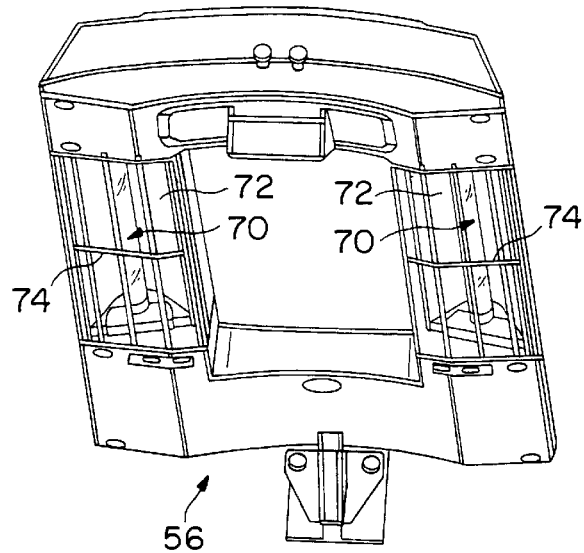
FIG. 5
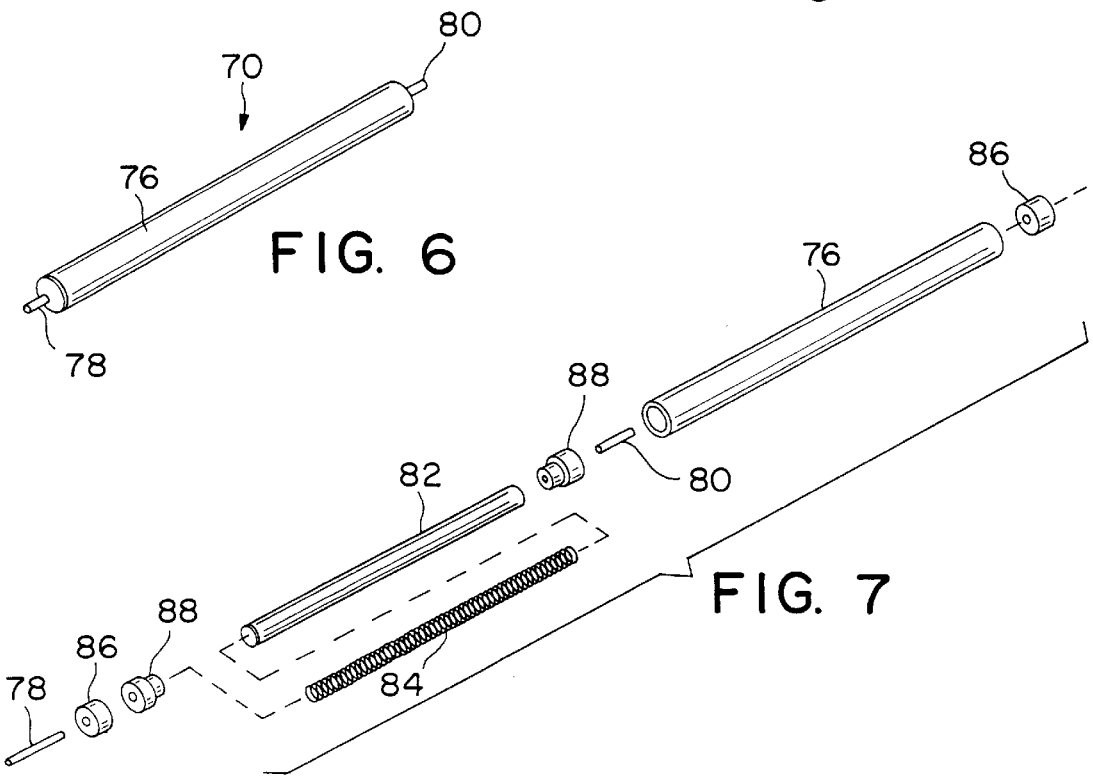
FIG. 6
FIG. 7

INFRARED HEATER APPARATUS

BACKGROUND AND SUMMARY OF THE INVENTION

The present invention relates to radiant heaters, and particularly to an infrared heater apparatus. More particularly, the present invention relates to an infrared heater apparatus for use on a thermal support device for maintaining a patient, such as an infant, at an appropriate temperature.

Incubators and radiant warmers have both been used to maintain the appropriate body temperature of small or premature infants. Radiant warmers provide for continuous and open access to an infant to accommodate a high frequency of intervention by the caregiver. Radiant warmers transfer heat to the patient via radiant heat transfer, typically from infrared heaters which emit infrared energy that is absorbed by the patient. The infrared heater is usually mounted to a support which is suspended above the patient support surface of the radiant warmer. See, for example, U.S. Pat. No. 5,162,038.

An incubator provides a generally transparent enclosure within which heated air is circulated to minimize the heat loss of the patient. In addition, heat is transferred to the patient via convective heat transfer. Incubators are typically provided with a large access door to allow for placement or removal of the infant in the incubator as well as supplemental access ways such as hand ports or small entry doors to permit routine care of the infant while minimizing heat loss from the incubator and the infant.

Incubators protect patients such as premature infants from exposure to ambient nursery contaminants in the form of noise and unfiltered air. Incubators provide mechanisms for filtering the air and raising the oxygen level within the incubator, as well as humidification mechanisms to control the relative humidity within the incubator. Patients such as infants or premature infants can often benefit from an oxygen-enriched atmosphere, because it reduces the amount of energy that must be expended by the patient in respiration, allowing the patient to maintain a lower metabolic rate. Patients with a variety of conditions, such as infections, elevated temperatures, or reduced amounts of hemoglobin, benefit from the oxygen-enriched atmosphere within the incubator.

U.S. Pat. No. 5,453,077 discloses an exemplary infant thermal support device that can function as either an incubator, a radiant warmer, or both. In the infant thermal support device of the '077 patent, air curtains cooperate with a patient-support surface to define a patient space that is protected from disturbances from outside of the patient space. The air curtains define an effective barrier to atmospheric influences outside of the patient space so that the patient space is generally unaffected by changes in the environment surrounding the patient thermal support device. At the same time, the patient thermal support device can be operated so that there are no physical barriers between the patient and the caregiver, providing the caregiver with continuous and open access to the patient even when the air curtains are in place.

The patient thermal support device of the '077 patent also includes an infrared radiant heater connected to the canopy to transfer heat to the patient via radiant heat transfer. The infrared radiant heater cooperates with the patient's own warmth, the warmed air that escapes the manifold to warm the patient support surface, and the warmed air of the air curtains delivered to the patient, to maintain the desired thermal environment for the patient. The radiant heater can help to achieve and maintain the desired patient temperature when neither the patient nor the warmed air are sufficient for attaining and maintaining the desired patient temperature.

The region of the electromagnetic radiation spectrum having wavelengths between about 760 and 1,000,000 nanometers (nm) is considered infrared radiant energy. Infrared A band includes wavelengths ranging from about 760–1,400 nm. Infrared B band includes wavelengths ranging from about 1,400–3,000 nm. Infrared C band includes wavelengths ranging from about 3,000–100,000 nm.

The infrared heater apparatus of the present invention is designed to minimize infrared radiation in the infrared A band. The infrared heater of the present invention emits substantially all of its radiant energy within the infrared B and C bands of the radiation spectrum.

Typical infrared heaters operate at very high temperatures ranging from about 1,100–1,200° C. and emit a red glow during operation. The glowing tube of a conventional infrared heaters can distort the color appearance of a child. Therefore, it is sometimes difficult to take an accurate color reading of an infant situated below a conventional infrared heater. The heater of the present invention operates at a substantially reduced temperature of about 300° C. to about 500° C. and does not glow. This facilitates taking accurate color readings of infants. The cooler heater of the present invention also reduces risks to the caregiver.

Since surface temperatures of the heater apparatus of the present invention are reduced, two such heaters are typically used in a patient thermal support device of the present invention to provide sufficient radiant energy to the support surface. Alternatively, a single heating element may be used having a larger diameter to produce larger emitting surface.

A common type of infrared heater used in infant radiant warmers is a "quartz tube" type, which comprises an infrared heat source contained within a quartz tube. An advantage to the quartz tube is that it is relatively transparent to infrared heat, allowing for rapid warm-up and cool-down of the infrared heater. Current quartz heaters are not sealed for use in an oxygen-enriched environment.

Another common type of heater used in infrared radiant warmers is known as a Cal-Rod™ type heater. These heaters have a wire heating element inside a metal sheath that is then packed densely with magnesium oxide. Cal-Rod™ type heaters reduce the potential for contact between the heating element and oxygen-enriched atmosphere.

However, the Cal-Rod™ heater provides only one seal around the heating element. If this single seal fails, the heating element would be exposed to the atmosphere. The Cal-Rod™ heater also has a relatively high thermal mass, requiring rather long warm-up and cool-down times when compared to the quartz heater design.

The present invention provides the quick warm-up and cool-down times of the quartz tube type heater and the safe operation in an oxygen-enriched atmosphere feature of the Cal-Rod™ type heater. The present invention provides an infrared heating device that minimizes the potential for contact between the heating element and the oxygen-enriched atmosphere, while also providing a relatively low thermal mass to allow for relatively short warm-up and cool-down times. The present invention also reduces emission of infrared A band wavelengths.

According to one aspect of the present invention, a radiant heater apparatus includes a heating element which generates radiant energy. The heating element has first and second terminals. The apparatus also includes an inner tube configured to surround the heating element. The inner tube includes first and second ends. The inner tube is substantially transmissive to radiant energy. The apparatus further includes an outer tube surrounding the inner tube. The outer tube has an inner surface, an outer surface, and first and second ends. The inner surface of the outer tube is absorptive to radiant energy, and the outer surface of the outer tube is emissive to radiant energy so that radiant energy from the heating element passing through the inner tube is absorbed and re-emitted from by outer tube.

In the illustrated embodiment, the outer tube is formed from metal such as stainless steel. The inner and outer surfaces of the outer tube are coated with an oxide material. The inner tube is formed from a quartz material. The heating element generates radiant energy with wavelengths having a first average length and the outer tube emits radiant energy with wavelengths having a second average length greater than the first average length.

In one illustrated embodiment, at least one spacer is located between the inner tube and the outer tube. Illustratively, the at least one spacer includes first and second silicone grommets located between the inner and outer tubes adjacent the first and second ends of the inner and outer tubes, respectively. First and second end caps coupled to the first and second ends of the inner tube, respectively.

In another illustrated embodiment for use in an oxygen enriched environment, first and second plugs are configured to be inserted into the first and second ends of the outer tube, respectively, to engage the inner surface of the outer tube and the inner tube to provide a seal between the outer tube, the inner tube, and the terminals of the heating element. First and second end caps are configured to be coupled to the first and second ends of the outer cylinder, respectively, to seal the outer cylinder and the first and second terminals of the heating element. The Association for Advancement of Medical Instruments (AAMI) requirements for heaters used in an oxygen-enriched environment require two separate fault conditions to occur before the heating element is exposed to the atmosphere.

The outer tube and the first and second end caps are illustratively made from a metal material. The first and second end caps are welded to the outer tube.

According to another aspect of the present invention, a patient warmer apparatus is provided for heating a patient on a patient support surface. The apparatus includes an infrared heater which emits a radiant energy output having wavelengths substantially within the infrared B and infrared C bands to minimize radiant energy emitted in the infrared A band.

Illustratively, the infrared heater emits radiant energy having a center spectrum with wavelengths between about 3,000–5,000 nm. The radiant heater has an output temperature of less than 1000° C., and illustratively between about 300° C. and about 500° C.

According to yet another aspect of the present invention, a patient thermal support apparatus includes a base, a patient support surface on the base, and a warmer module coupled to the base spaced apart from the patient support surface. The warmer module includes first and second infrared heaters which emit infrared radiant energy, the first and second heaters each having an operating temperature less than 1000° C. Illustratively, the first and second radiant heaters each have an output temperature of about 300° C. to about 500° C. and do not emit a red glow like conventional infrared heaters.

Illustratively, the first and second radiant heaters each emit a radiant energy output having wavelengths substantially within the infrared B and infrared C bands to minimize radiant energy emitted in the infrared A band. The first and second infrared heaters each emit radiant energy having a center spectrum with wavelengths between about 3,000–5,000 nm.

Additional objects, features, and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 5 is a perspective view of a canopy of the patient thermal support device of FIG. 4 including first and second radiant heaters of the second embodiment of the present invention which are designed for use in an oxygen-enriched environment;

FIG. 6 is a perspective view of one of the radiant heaters of FIG. 5;

FIG. 7 is an exploded perspective view illustrating the elements of the radiant heater of FIG. 6;

DETAILED DESCRIPTION OF THE DRAWINGS

Figure 1:
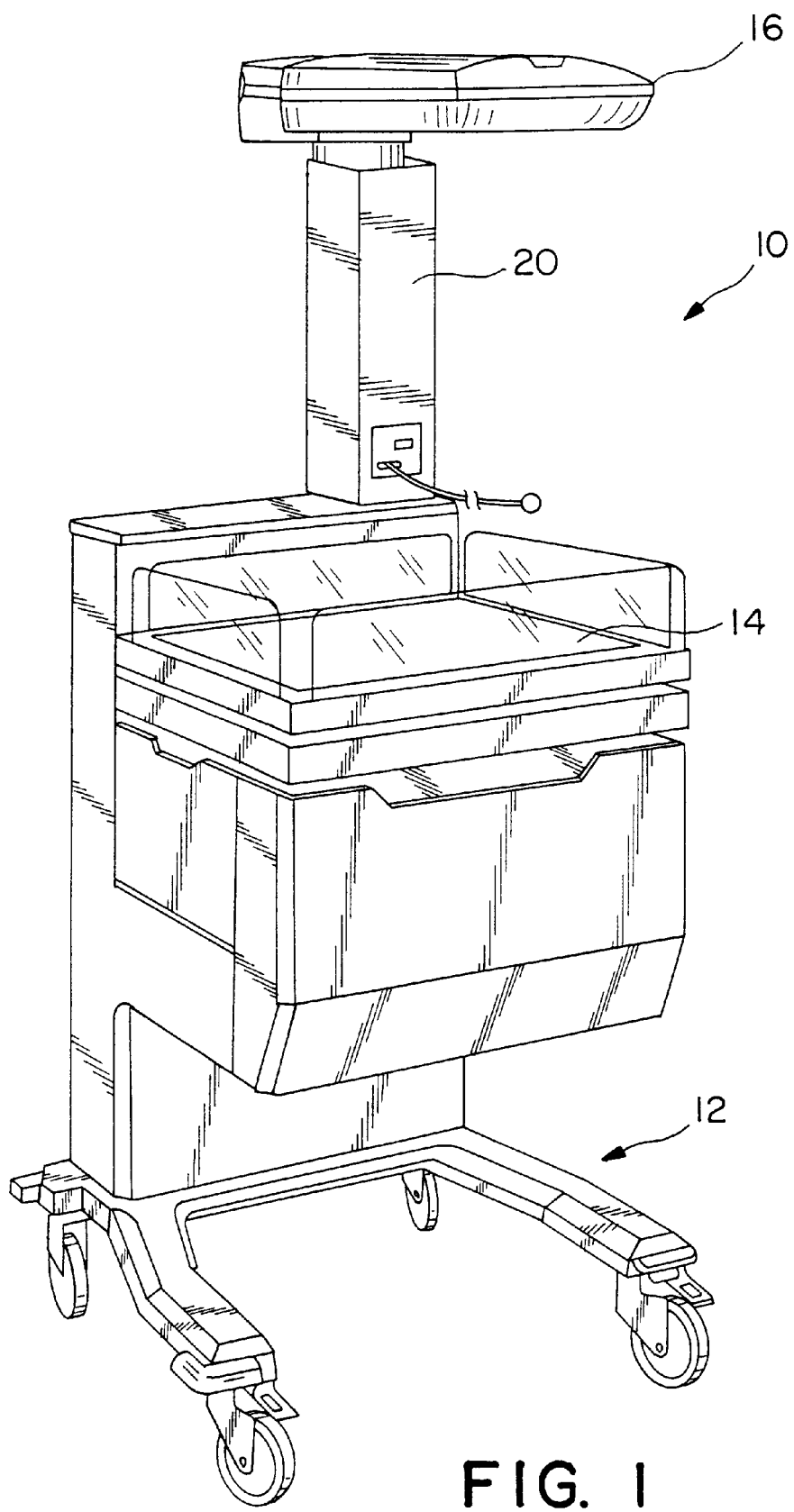
FIG. 1 is a perspective view of a patient thermal support device including a radiant heater apparatus of a first embodiment of the present invention.

Referring now to the drawings, FIG. 1 illustrates a patient thermal support device 10 including a base 12, a patient support surface 14, and a warmer and lighting module 16 spaced above the patient support surface 14. Such infant thermal support devices are generally known. See, for example, U.S. Pat. No. 5,162,038.

Figure 2:
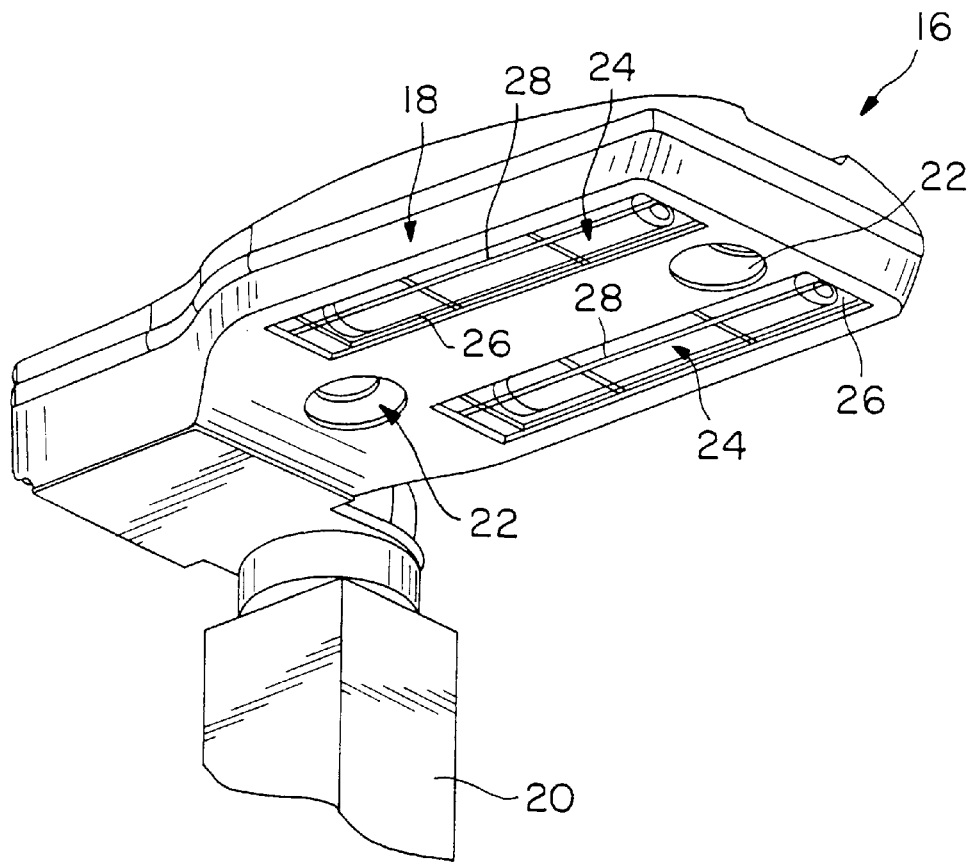
FIG. 2 is a perspective view of a warmer and lighting module of FIG. 1 which includes a pair of radiant heaters of the present invention.

The warmer and lighting module 16 of the present invention is further illustrated in FIG. 2. The module 16 includes a housing 18 rotatably coupled to a support 20. Lights 22 are coupled to housing 18. In addition, a pair of infrared heaters 24 are also located within housing 18. Illustratively, infrared heaters 24 are located within parabolic reflectors 26 and covered by protective grates 28.

The infrared heaters 24 of the present invention are configured to emit infrared radiant energy substantially in the infrared B and C bands, while minimizing radiant energy in the infrared A band. Conventional infrared heaters, such as quartz heaters, operate at very high temperatures (1,100–1,200° C.) and glow during operation. The heaters 24 of the present invention operate at a reduced surface temperature (about 300° C. to about 500° C.) compared to temperatures of conventional infrared heaters. Therefore, two infrared heaters 24 are used to provide sufficient radiant energy to the patient support surface 14. Since the infrared heaters 24 of the present invention do not glow, the heaters 24 do not distort the color of the infant located on the patient support surface 14.

Figure 3:
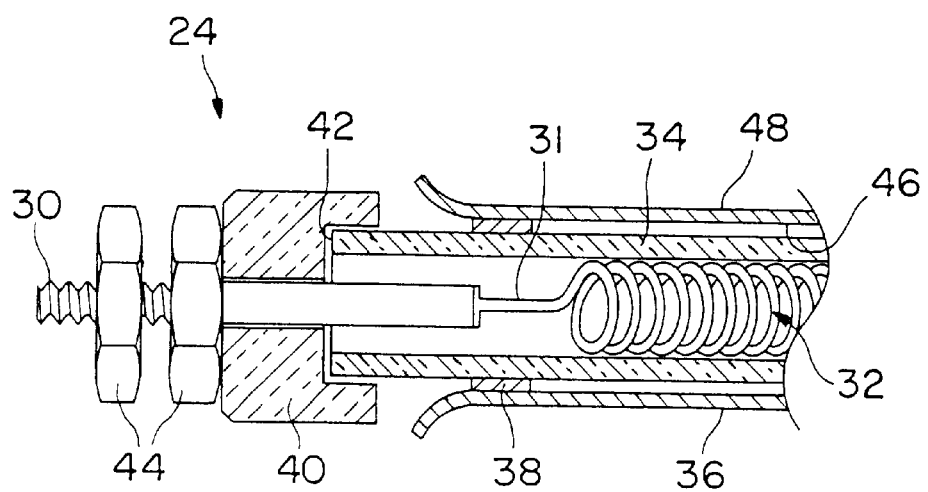
FIG. 3 is a sectional view taken through a portion of one of the infrared heaters of FIG. 2.
Figure 3A:
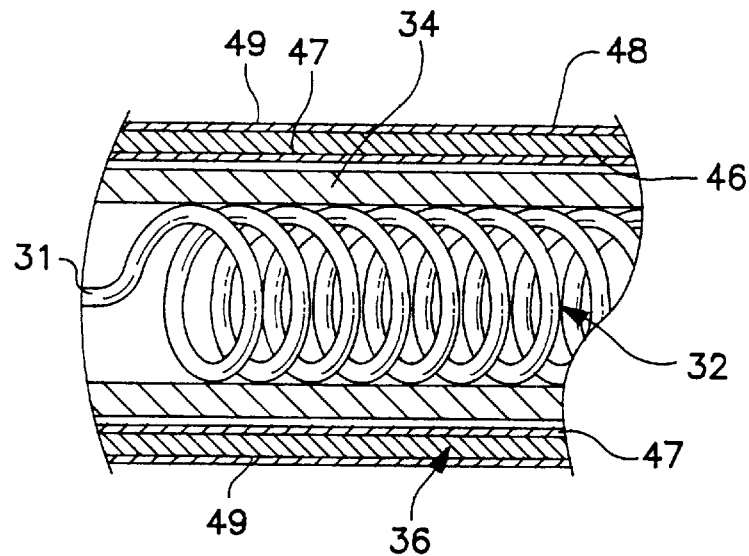
FIG. 3A is an enlarged view of a portion of FIG. 3 illustrating coatings on inner and outer surfaces of an outer container.
Figure 8A:
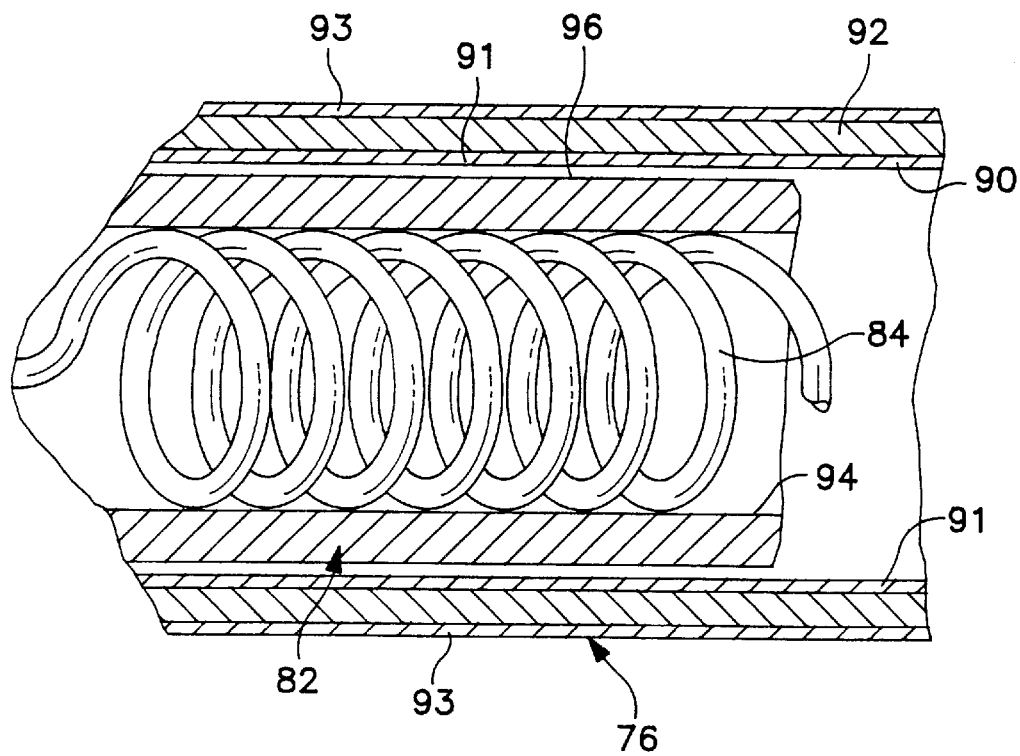
FIG. 8A is an enlarged view of a portion of FIG. 8 illustrating coatings on inner and outer surfaces of an outer container.

Details of the infrared heater 24 are illustrated in FIG. 3. One end of heater 24 is shown. The other end (not shown) is mirror symmetrical to the illustrated end.

The heater 24 includes a threaded terminal 30 at each end of the heater. Terminal 30 is coupled to an end 31 of a coiled heater element 32. Illustratively, heater element 32 is a Ni-Cr heater element. A quartz tube 34 surrounds the heater element 32.

A metallic outer tube 36 surrounds the quartz tube 34. Illustratively, metallic tube 36 is a stainless steel tube having a uniform, oxidized layer on both its inner surface 46 and outer surface 48. A silicone grommet 38 is located between quartz tube 34 and metallic tube 36 at each end of the heater 24 to provide spacing between tubes 34 and 36. A ceramic cap 40 is located over each end 42 of quartz tube 34. Hex nuts 44 are located on each threaded terminal 30 to secure the ceramic cap 40 to the heater element 24.

In operation, the coil 32 of heater 24 is heated in a conventional manner by passing electricity through the coil 32. Coil 32 generates radiant energy, a substantial component of which is in the infrared A band. The emitted radiant energy passes through the quartz tube 34. It is understood that other materials may be used in place of the quartz tube 34. These materials must have a high transmissivity for infrared radiation. The material of inner tube 34 must also be made from an electrically insulated material.

The radiant energy passing through quartz tube 34 is absorbed by a coating 47 on inner surface 46 of metallic tube 36. Illustratively, the coating 47 on inner surface 46 is a black oxide layer formed by heating the stainless steel tube 36. It is understood that other methods of treatment or coatings which have a high absorptivity may be used on the inner surface 46 of metallic tube 36. For instance, a suitable flat paint may be used, if desired.

Metallic tube 36 includes a coating 49 having a high emissivity on outer surface 48 of metallic tube 36. Radiant energy absorbed by the metallic tube 36 is re-emitted at as infrared B and C band wavelengths. The outer layer coating 49 on tube 36 is illustratively a black oxide layer formed on a stainless steel tube 36 by heating the tube. However, it is understood that other methods of treatment or coatings which have high emissivity may be used. For instance, a suitable flat paint may be used, if desired.

Stainless steel was selected as the illustrated embodiment since stainless steel permits formation of a thin outer wall while maintaining strength. In addition, the black oxide layer on inner wall 46 and outer wall 48 is easily formed by heating the stainless steel tube 36. It is understood that other types of metallic tubes may be used such as aluminum, carbon steel, copper, etc.

Typically, the coil 32 which passes through quartz heater 34 is at a temperature of about 1,100–1,200° C. Such quartz heaters are of the type typically used in conventional radiant warmers for patient thermal support devices. Heater 24 of the present invention which absorbs the radiant energy from coil 32 and then re-emits the radiant energy from tube 36 operates at a temperature of about 300° C. to about 500° C. Therefore, the output temperature from heater 24 is substantially reduced. Since lower temperatures are generated, two heaters 24 are typically required to warm the patient on the patient support surface 14. Heater 24 has a relatively low thermal mass to provide relatively short warm-up times and cool-down times Positioning the quartz tube 34 within the outer metal tube 36 increases the wavelengths of radiant energy emitted from heater 24. The radiant energy emitted by heater 24 is illustratively centered at wavelengths between about 3,000–5,000 nm, which is in the infrared C band spectrum. Therefore, the infrared heater 24 of the present invention operates at a higher wave length and a lower temperature than conventional infrared heaters used in patient thermal support devices. Heater 24 minimizes emission of radiant energy in the infrared A band.

Figure 4:
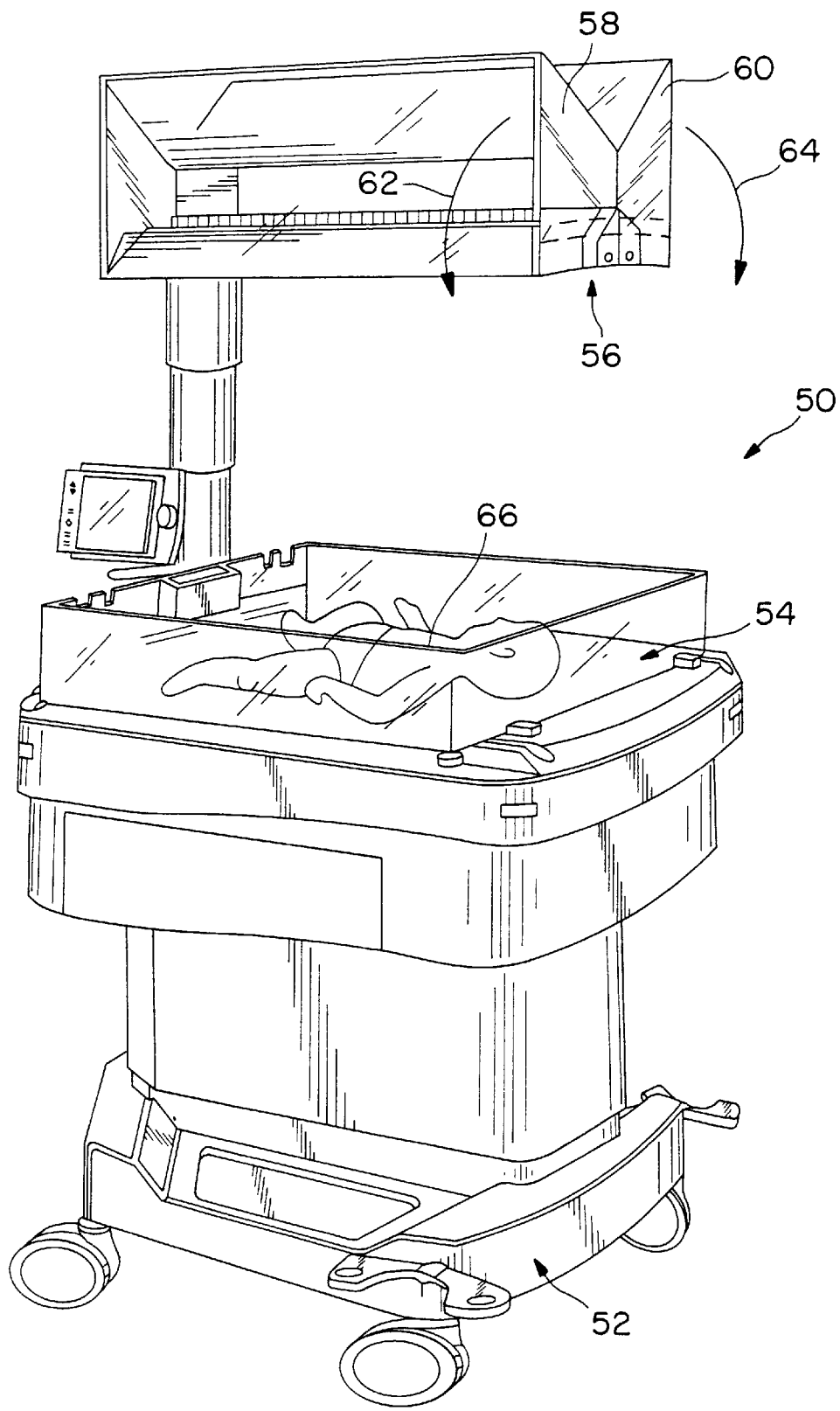
FIG. 4 is a perspective view of another patient thermal support apparatus which also provides a flow of air and/or oxygen near the patient including a second embodiment of the radiant heater of the present invention for use in an oxygen-enriched environment.

Another patient thermal support device 50 is illustrated in FIG. 4. The thermal support device 50 includes a base 52, a patient support surface 54, and a canopy 56. Such patient thermal support devices are generally known. See, for example, U.S. Pat. No. 5,453,077.

The canopy 56 includes a pair of pivoting sections 58 and 60 which pivot downwardly in the directions of arrows 62 and 64, respectively, to provide a top enclosure. Air curtains can be generated to isolate the patient 66. Oxygen may also be supplied to the patient 66 to generate an oxygen-enriched environment. Such an environment is typically has at least 4% greater oxygen levels than ambient air.

Figure 8:
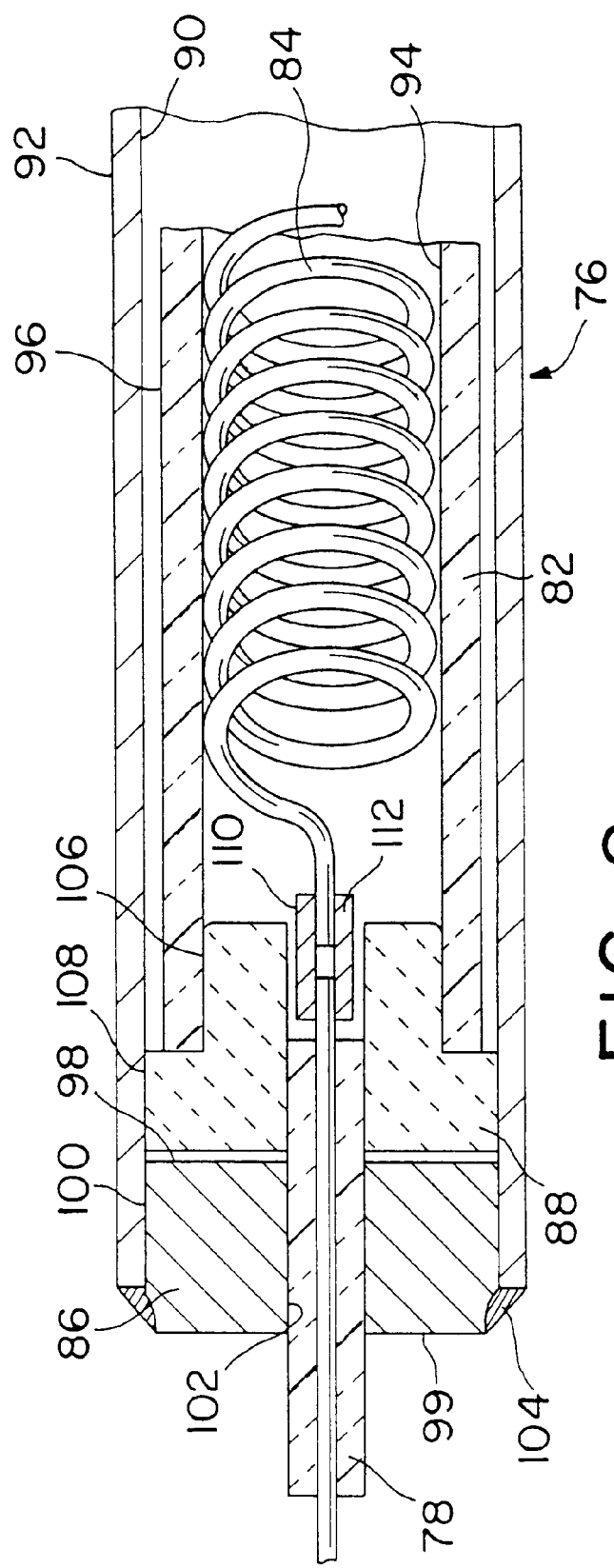
FIG. 8 is a sectional view taken through the radiant heater of FIG. 6 illustrating further details of the second embodiment of the radiant heater.
Figure 9:
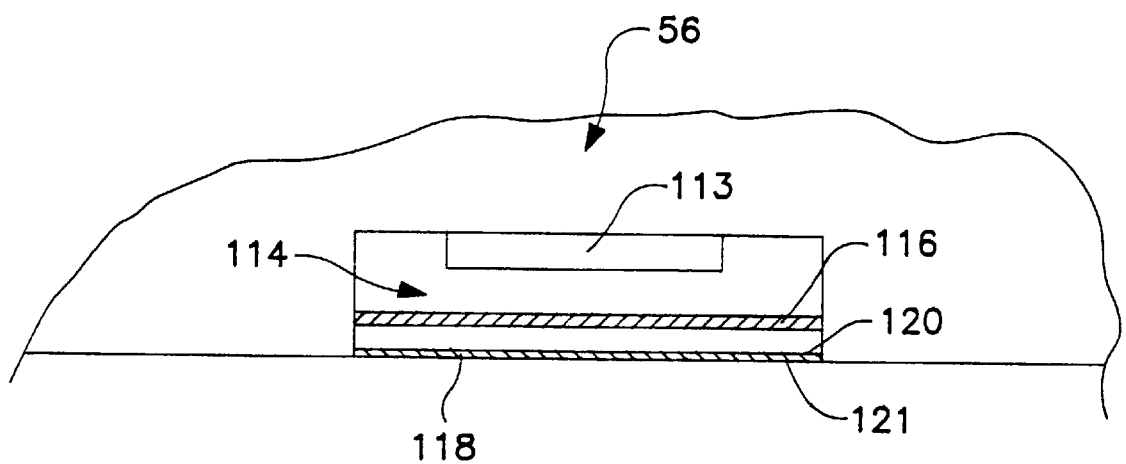
FIG. 9 is a diagrammatic view of another embodiment of the present invention in which a heater coil is located in a recess of a canopy with a sheet of transmissive material sealed to the canopy over the coil and a sheet of metal material having an absorptive inner surface and an emissive outer surface sealed to the canopy over the transmissive sheet.

FIG. 5 illustrates a bottom portion of canopy 56 with side members 58 and 60 removed. Two spaced apart infrared heaters 70 are located within parabolic reflectors Grates 74 are located over the heaters 70. The infrared heaters 70 are best illustrated in FIGS. 6–8. Heaters 70 are designed for use in an oxygen-enriched environment.

FIG. 6 is a perspective view of a preferred embodiment of the infrared heating device 70 in its assembled form. The heater 70 includes an outer tube or container 76 into which pass an insulated power supply terminal 78 and an insulated power return terminal 80. Referring to FIG. 7, the heater 70 further incudes an inner tube or container 82 into which the power supply wire 78 and power return wire 80 pass, and a nickel-chromium (Ni-Cr) electric heating coil 84 located within the inner container 82. The power supply terminal 78 connects to one end of the heating coil 84 and the power return wire 80 connects to the other end.

Referring to FIGS. 7 and 8, the heater 70 of the present invention, includes two end caps 86 for sealing the outer container 76 and two plugs 88 for sealing the inner container 82. The outer container 76 is formed as a thin-walled metal cylinder with an inside surface 90, an outside surface 92, and openings at each end. The outer container 76 of the illustrated embodiment is fabricated from thin-walled stainless steel (illustratively from about 0.015 inches (0.0059 cm) to about 0.020 inches (0.0078 cm) thick) in order to provide a relatively low thermal mass. The invention contemplates forming the outer container 76 from any material which can withstand the temperatures generated by the infrared heating element 84 while providing a relatively low thermal mass. For example, aluminum, copper, carbon steel, etc. may be used.

The outer container 76 is further coated on its inside surface 90 with a high absorptivity coating 91 and coated on its outside surface 92 with a high emissivity coating 91,93. Illustratively the coatings are black oxide coating 93. Although the preferred embodiment employs thin-walled metal with a high emissivity coating, the invention contemplates other implementations such as an outer container 76 formed from a material which is inherently highly emissive, thereby obviating the need for a separate high emissivity coating.

The inner container 82 of the preferred embodiment of the present invention is formed as a cylinder with an inside surface 94, an outside surface 96, and openings at each end. The diameter of the inner container 82 is such that the inner container outside surface 96 fits within the outer container 76 inside surface 90, and the length of inner container 82 is less than the length of outer container 76. The inner container 82 of is illustratively fabricated from quartz, which desirably is relatively transparent to infrared heat generated from the nickel-chromium heating coil 84. Other materials with a high transmissivity may be used for inner container 82.

Each end cap 86 has a circular face 98 and a cylindrical side wall 100 sized so that the cylindrical side wall 100 fits snugly within the inside surface 90 of the outer container 76. Each end cap 86 is further formed with a circular opening 102 sized so that the insulated power supply terminal 78 or power return terminal 80 fit through the openings 102. Terminals 78, 80 are coupled to heating element 84 by connectors 112. After the terminals 78, 80 are installed through the end caps 86, one end cap 86 is swaged around the power supply terminal 78 and the other end cap 86 is swaged around power return terminal 80 to create an atmospheric seal between the end caps 86 and the terminals 78, 80 around the circular openings 102. In the illustrated embodiment, the end caps 86 are each then sealed to the outer container 76 with a weld 104 around the circular faces 99 of the end caps 86. The welds 104 thereby complete an atmospheric seal of the outer container 76. The end caps 86 in the illustrated embodiment are formed from the same material as the outer container 76, for example, stainless steel, aluminum, or other suitable metal.

Still referring to FIGS. 7 and 8, each plug 88 has an inner cylindrical section 106 and an outer cylindrical section 108. The plugs 88 are formed from a compressible material, such as silicone in the illustrated embodiment. The inner cylindrical section 106 is sized to fit snugly within the inner surface 94 of the inner container 82. The outer cylindrical section 108 is sized to fit snugly within the inner surface 90 of the outer container 76. Each plug 88 is further formed with a circular opening 110 sized to allow passage of the insulated power supply terminals 78 or power return terminals 80 through the plug 88. When the insulated terminals 78, 80 are inserted through the openings 110 of the plugs 88 and the plugs 88 are inserted into the openings of the inner container 82, the plugs 88 compress to form atmospheric seals between the plugs 88 and the inner surface 94 of the inner container 82, between the plugs 88 and the inner surface 90 of the outer container 76, and between the plugs 88 and the insulated terminals 78, 80. The plugs 80 further advantageously retain the inner container 82 centered within the outer container 76. Although the plugs 88 are formed from silicone in the preferred embodiment, the invention contemplates other suitable compressible, heat resistant materials.

The assembled heater 70 thus provides an infrared heating element in a first sealed container located within a second sealed container. Each sealed container allows passage of the power supply and return terminals 78 and 80 for the heating element through the container while maintaining an atmospheric seal within the container. The sealed chamber within a sealed chamber design meets AAMI requirements for use in an oxygen-enriched environment. As discussed above with reference to the first embodiment, the inner container 82 is relatively transmissive to the infrared heat source and electrically insulated and the outer container 82 has a relatively low thermal mass. The heating device thereby provides for relatively quick warm-up and cool-down times.

It is understood that other sealed heaters may be used. For instance a heater coil 113 may be located within a recess 14 of warmer module 16 or canopy 56. A sheet 116 of transmissive material may then be sealed to canopy 56 over the coil. A sheet 118 of metal material having an absorptive inner surface 120 and an emissive outer surface 121 may then be sealed to the canopy 56 over the transmissive sheet.

Although the invention has been described in detail with reference to certain preferred embodiments, variations and modifications exist within the scope and spirit of the invention as described and defined in the following claims.

What is claimed is:

1. A radiant heater apparatus comprising:
   a heating element which generates radiant energy, the heating element having first and second terminals;
   an inner tube configured to surround the heating element, the inner tube including first and second ends, and the inner tube being substantially transmissive to radiant energy;
   an inner atmospheric seal coupled to each of the first and second ends of the inner tube:
   an outer tube surrounding the inner tube, the outer tube having an inner surface, an outer surface, and first and second ends, the inner surface of the outer tube being absorptive to radiant energy, and the outer surface of the outer tube being emissive to radiant energy so that radiant energy from the heating element passing through the inner tube is absorbed and re-emitted by the outer tube; and
   an outer atmospheric seal coupled to each of the first and second ends of the outer tube, whereby the heating element remains sealed from the atmosphere upon a failure of one of the inner and outer atmospheric seals.

2. The apparatus of claim 1, wherein the outer tube is formed from metal.

3. The apparatus of claim 2, wherein the outer tube is formed from stainless steel.

4. The apparatus of claim 2, wherein the outer tube is formed from aluminum.

5. The apparatus of claim 2, wherein the inner and outer surfaces of the outer tube are coated with an oxide material.

6. The apparatus of claim 1, wherein the inner tube is formed from a quartz material.

7. The apparatus of claim 1, further comprising first and second plugs configured to be inserted into the first and second ends of the outer tube, respectively, to engage the inner surface of the outer tube and the inner tube to provide a seal between the outer tube, the inner tube, and the terminals of the heating element.

8. The apparatus of claim 7, further comprising first and second end caps configured to be coupled to the first and second ends of the outer cylinder, respectively, to seal the outer cylinder and the first and second terminals of the heating element.

9. The apparatus of claim 8, wherein the outer tube and the first and second end caps are made from a metal material.

10. The apparatus of claim 9, wherein the first and second end caps are welded to the outer tube.

11. The apparatus of claim 1, further comprising at least one spacer located between the inner tube and the outer tube.

12. The apparatus of claim 11, wherein the at least one spacer includes first and second silicone grommets located between the inner and outer tubes adjacent the first and second ends of the inner and outer tubes, respectively.

13. The apparatus of claim 11, further comprising first and second end caps coupled to the first and second ends of the inner tube, respectively.

14. The apparatus of claim 1, wherein the heating element has a temperature greater than 1000° C., and the outer tube has a temperature outside its outer surface of less than 750° C.

15. The apparatus of claim 14, wherein the temperature of the outer tube outside its outer surface of the outer tube is between about 300° C. and about 500° C.

16. The apparatus of claim 1, wherein the heating element generates radiant energy with wavelengths having a first average length and the outer tube emits radiant energy with wavelengths having a second average length greater than the first average length.

17. The apparatus of claim 16, wherein the heating element generates radiant energy having wavelengths substantially in the infrared A band, and the outer tube emits radiant energy having wavelengths substantially within the infrared B and infrared C bands to minimize radiant energy emitted in the infrared A band.

18. The apparatus of claim 17, wherein the outer tube emits radiant energy having a center spectrum with wavelengths between about 3000–5000 nm.

19. The heating device of claim 1, wherein the heating element is a coiled nickel-chromium wire.

20. A radiant heating device comprising:
a heating element having a power supply terminal and a power return terminal;
a first container configured to receive the heating element, the first container having an egress for the power supply terminal and power return terminal;
first sealing means for sealing the egress from the first container so that the first chamber is impervious to oxygen to provide an inner oxygen seal around the heating element;
a second container configured to receive the first container, the second container having an egress for the power supply terminal and power return terminal; and
a second sealing means for sealing the egress from the second container so that the second chamber is impervious to oxygen to provide an outer oxygen seal around the first container.

21. The heating device of claim 20, wherein the heating element is an infrared heat source.

22. The heating device of claim 21, wherein the heating element is a coiled nickel-chromium wire.

23. The heating device of claim 20, wherein the power supply wire and power return wire are insulated with silicone.

24. The heating device of claim 20, wherein the first container is a quartz cylinder having a first opening at a first end and a second opening at a second end.

25. The heating device of claim 20, wherein the second container is a cylinder having a first opening at a first end and a second opening at a second end.

26. The heating device of claim 20, wherein the second container is made of metal.

27. The heating device of claim 26, wherein the second container is made of aluminum.

28. The heating device of claim 26, wherein the second container is made of stainless steel.

29. The heating device of claim 26, wherein at least a portion of both an inner surface and an outer surface of the second container are coated with an oxide material.

30. The heating device of claim 26, wherein the cylinder wall of the second container is about 0.015 inches to about 0.02 inches thick.

31. The heating device of claim 25, wherein the second sealing means includes first and second end caps, the first end cap sized to engage the first opening of the second container and having an egress sized to receive and seal the power supply terminal, the second end cap sized to engage and seal the second opening of the second container and having an egress sized to receive and seal the power return terminal.

32. The heating device of claim 31, wherein the second container is made of metal.

33. A patient thermal support apparatus comprising:
a base;
a patient support surface on the base; and
a warmer module coupled to the base spaced apart from the patient support surface, the warmer module including first and second infrared heaters which emit infrared radiant energy, the first and second heaters each having an operating temperature of about 300° C. to about 500° C.

34. The apparatus of claim 33, wherein the first and second radiant heaters each emit a radiant energy output having wavelengths substantially within the infrared B and infrared C bands to minimize radiant energy emitted in the infrared A band.

35. The apparatus of claim 34, wherein the first and second infrared heaters each emit radiant energy having a center spectrum with wavelengths between about 4,000–5,000 nm.

36. A patient thermal support apparatus for use in an oxygen enriched environment, the apparatus comprising:
a base;
a patient support surface on the base; and
a warmer module coupled to the base spaced apart from the patient support surface, the warmer module including a housing having a recessed portion, a heating element which generates radiant energy located in the recessed portion, a first sealed member located over the heating element to provide an inner oxygen seal around the heating element, the first sealed member being substantially transmissive to radiant energy, and a second sealed member located over the first sealed member to provide an outer oxygen seal around the first sealed member, the second sealed member having an inner surface which is absorptive to radiant energy, and outer surface which is emissive to radiant energy so that radiant energy from the heating element passing through the first sealed member is absorbed and re-emitted by the second sealed member.

37. The apparatus of claim 36, wherein the first sealed member is an inner tube configured to surround the heating element, and the second sealed member is an outer tube surrounding the inner tube.

38. A patient thermal support apparatus for use in an oxygen enriched environment, the apparatus comprising:
a base;
a patient support surface on the base; and a warmer module coupled to the base spaced apart from the patient support surface, the warmer module including a housing having a recessed portion, a heating element which generates radiant energy located in the recessed portion, a first sealed member located over the heating element, the first sealed member being substantially transmissive to radiant energy, and a second sealed member located over the first sealed member, the second sealed member having an inner surface which is absorptive to radiant energy, and outer surface which is emissive to radiant energy so that radiant energy from the heating element passing through the first sealed member is absorbed and re-emitted by the second sealed member, the first sealed member being a first sheet material sealed to the warmer module housing over the heating element, and the second sealed member being a second sheet material sealed to the warmer module housing over the first sheet material.

39. A radiant heating device comprising:

a heating element having a power supply terminal and a power return terminal;

a quartz cylinder configured to receive the heating element, the quartz cylinder having a first opening at a first end and a second opening at a second end;

first and second resilient plugs configured to seal the first and second openings of the quartz cylinder so that the quartz cylinder is impervious to oxygen, the first plug being configured to seal the first opening of the quartz cylinder and having an egress sized to receive and seal the power supply terminal, the second plug being configured to seal the second opening of the quartz cylinder and having an egress sized to receive and seal the power return terminal;

a second container configured to receive the quartz cylinder, the second container configured to absorb and retransmit heat energy from the heating element and having an egress for the power supply terminal and power return terminal; and means for sealing the egress from the second container so that the second chamber is impervious to oxygen.

40. The heating device of claim 39, wherein the plugs are further formed to engage a surface of the second container causing the quartz cylinder to be held at a fixed position within the second container.

41. The heating device of claim 39, wherein the resilient plugs are formed from silicone.

42. A radiant heating device comprising:

a heating element having a power supply terminal and a power return terminal;

a first container configured to receive the heating element, the first container having an egress for the power supply terminal and power return terminal;

means for sealing the egress from the first container so that the first chamber is impervious to oxygen;

a second container configured to receive the first container, the second container having a first opening at a first end and a second opening at a second end defining an egress for the power supply terminal and the power return terminal, respectively; and first and second end caps, the first end cap being sized to engage and seal the first opening of the second container and having an egress sized to receive and seal the power supply terminal, the second end cap being sized to engage and seal the second opening of the second container and having an egress sized to receive and seal the power return terminal, the first end cap being swaged around the power supply terminal and the second end cap being swaged around the power return terminal.

43. A radiant heating device comprising:

a heating element having a power supply terminal and a power return terminal;

a first container configured to receive the heating element, the first container having an egress for the power supply terminal and power return terminal;

means for sealing the egress from the first container so that the first chamber is impervious to oxygen;

a second container configured to receive the first container, the second container having a first opening at a first end and a second opening at a second end defining an egress for the power supply terminal and the power return terminal, respectively; and first and second end caps, the first end cap being sized to engage and seal the first opening of the second container and having an egress sized to receive and seal the power supply terminal, the second end cap being sized to engage and seal the second opening of the second container and having an egress sized to receive and seal the power return terminal, the first end cap being welded around the power supply terminal and the second end cap being welded around the power return terminal.

44. The heating device of claim 20, wherein the second container includes an inner surface absorptive to radiant energy and an outer surface emissive to radiant energy so that radiant energy from the heating element passing through the inner container is absorbed and re-emitted by the outer container.

\* \* \* \* \*